(12) United States Patent
Seel (10) Patent No.: US 9,005,239 B2
(45) Date of Patent: Apr. 14, 2015

(54) MEDICAL INSTRUMENT

(71) Applicant: Aesculap AG, Tuttlingen (DE)

(72) Inventor: Wilhelm Seel, Stockach (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 14/266,037

(22) Filed: Apr. 30, 2014

(65) Prior Publication Data

US 2014/0296858 A1    Oct. 2, 2014

Related U.S. Application Data

(63) Continuation of application No. PCT/EP2012/072937, filed on Nov. 17, 2012.

(30) Foreign Application Priority Data

Dec. 9, 2011 (DE) .......................... 10 2011 056 235

(51) Int. Cl.
| | |
|---|---|
| *A61B 17/00* | (2006.01) |
| *A61B 17/16* | (2006.01) |
| *A61B 17/28* | (2006.01) |
| *A61B 17/29* | (2006.01) |
| *A61B 19/00* | (2006.01) |

(52) U.S. Cl.
CPC ......... *A61B 17/1606* (2013.01); *A61B 17/1611* (2013.01); *A61B 17/2816* (2013.01); *A61B 17/2909* (2013.01); *A61B 2017/0046* (2013.01); *A61B 2017/2845* (2013.01); *A61B 2017/292* (2013.01); *A61B 2019/4868* (2013.01)

(58) Field of Classification Search
USPC .................................................... 606/208, 83
See application file for complete search history.

(56) References Cited

U.S. PATENT DOCUMENTS

| 3,777,538 A | 12/1973 | Weatherly et al. |
|---|---|---|
| 3,814,102 A | 6/1974 | Thal |
| 4,043,343 A | 8/1977 | Williams |
| 4,369,788 A | 1/1983 | Goald |

(Continued)

FOREIGN PATENT DOCUMENTS

| DE | 356 185 | 7/1922 |
|---|---|---|
| DE | 69 35 459 | 1/1970 |

(Continued)

*Primary Examiner* — Sameh Boles
(74) *Attorney, Agent, or Firm* — Lipsitz & McAllister, LLC (57) ABSTRACT

The invention relates to a medical instrument comprising at least one movable tool element and at least one actuating element which is mounted such as to be pivotal about a pivotal axis and is coupled to the at least one tool element for the purposes of moving the tool element as a result of a pivotal movement of the actuating element, wherein, for the pivotal mounting of the at least one actuating element, there is provided a pivotal bearing comprising a bearing shaft holder and a bearing shaft which is held in the bearing shaft holder in a working position, wherein the at least one actuating element incorporates the bearing shaft or the bearing shaft holder, wherein the bearing shaft holder has an insertion opening and is insertable through the insertion opening into the bearing shaft holder in a direction that is transverse or substantially transverse to the pivotal axis.

23 Claims, 6 Drawing Sheets

(56) References Cited

U.S. PATENT DOCUMENTS

| | | |
|---|---|---|
| 4,440,170 A | 4/1984 | Golden et al. |
| 5,336,238 A | 8/1994 | Holmes et al. |
| 5,368,606 A | 11/1994 | Marlow et al. |
| 5,385,570 A | 1/1995 | Chin et al. |
| 5,507,774 A | 4/1996 | Holmes et al. |
| 5,584,844 A * | 12/1996 | Weisshaupt .................. 606/170 |
| 2005/0120566 A1 | 6/2005 | Dworschak et al. |

FOREIGN PATENT DOCUMENTS

| | | |
|---|---|---|
| DE | 43 16 768 | 11/1994 |
| DE | 296 01 208 | 4/1996 |
| DE | 298 22 166 | 3/1999 |
| DE | 20 2009 002 235 | 8/2009 |
| WO | WO 01/35838 | 5/2001 |
| WO | WO 03/094756 | 11/2003 |

\* cited by examiner

MEDICAL INSTRUMENT

CROSS-REFERENCE TO RELATED APPLICATIONS

This application is a continuation of international application number PCT/EP2012/072937 filed on Nov. 17, 2012 and claims the benefit of German application number 10 2011 056 235.4 filed on Dec. 9, 2011 which are incorporated herein by reference in their entirety and for all purposes.

FIELD OF THE INVENTION

The present invention relates to medical instruments generally, and more specifically to a medical instrument comprising at least one movably arranged tool element and at least one actuating element which is mounted such as to be pivotal about a pivotal axis and is directly or indirectly coupled to the at least one tool element for the purposes of moving the tool element as a result of a pivotal movement of the actuating element, wherein, for the pivotal mounting of the at least one actuating element, there is provided a pivotal bearing comprising a bearing shaft holder and a bearing shaft which is held in the bearing shaft holder in a working position, wherein the at least one actuating element incorporates the bearing shaft or the bearing shaft holder.

BACKGROUND OF THE INVENTION

Medical instruments of the type described hereinabove are known in various forms. The pivotal bearing of one or more actuating elements of the instruments is usually realized in that the bearing shaft holder is in the form of a bore into which the bearing shaft is slid coaxially with respect to the longitudinal axis defined thereby and is fixed by riveting, a swelling process or by means of a screw connection for example. The disadvantage of this however are the high assembly costs associated with the construction of the pivotal bearing.

SUMMARY OF THE INVENTION

In a first aspect of the invention, a medical instrument comprises at least one movable tool element and at least one actuating element which is mounted such as to be pivotal about a pivotal axis and is directly or indirectly coupled to the at least one tool element for the purposes of moving the tool element as a result of a pivotal movement of the actuating element. For the pivotal mounting of the at least one actuating element, there is provided a pivotal bearing comprising a bearing shaft holder and a bearing shaft which is held in the bearing shaft holder in a working position. The at least one actuating element incorporates the bearing shaft or the bearing shaft holder. The bearing shaft holder has an insertion opening. In an assembly position, the bearing shaft is insertable through the insertion opening into the bearing shaft holder in a direction that is transverse or substantially transverse to the pivotal axis.

BRIEF DESCRIPTION OF THE DRAWINGS

The following description of preferred embodiments of the invention will serve, in conjunction with the drawings, to provide a more detailed explanation. Therein.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrument comprising at least one movable tool element and at least one actuating element which is mounted such as to be pivotal about a pivotal axis and is directly or indirectly coupled to the at least one tool element for the purposes of moving the tool element as a result of a pivotal movement of the actuating element, wherein, for the pivotal mounting of the at least one actuating element, there is provided a pivotal bearing comprising a bearing shaft holder and a bearing shaft which is held in the bearing shaft holder in a working position, wherein the at least one actuating element incorporates the bearing shaft or the bearing shaft holder, wherein the bearing shaft holder has an insertion opening and wherein, in an assembly position, the bearing shaft is insertable through the insertion opening into the bearing shaft holder in a direction that is transverse or substantially transverse to the pivotal axis.

In particular, the development proposed in accordance with the invention enables the bearing shaft to be arranged or formed on the at least one actuating element or on the instrument including being formed in one piece manner with the instrument or the at least one actuating element for example, and, for the purposes of assembling the instrument, simply introducing the bearing shaft into the bearing shaft holder by inserting it through the insertion opening. Further elements, tools or working steps, such as are necessary in the known instruments in order to form a fitting of two mutually pivotal parts of the instrument, are not then required for the assembly of the at least one actuating element on the instrument. After the insertion of the bearing shaft into the bearing shaft holder, the at least one actuating element can be pivoted, especially directly, about the pivotal axis in order to directly or indirectly move the at least one tool element in a desired manner as a result of such a pivotal movement.

It is advantageous if the bearing shaft that has been inserted into the bearing shaft holder is movable from the assembly position into the working position in which the bearing shaft is held captive in the bearing shaft holder by pivoting it about the pivotal axis. This permits the specially formed bearing shaft holder together with the bearing shaft in particular to be designed in such a way that the bearing shaft is insertable into the bearing shaft holder firstly by means of a purely translatory movement whereafter it is movable by means of a pivotal movement into the working position in which the bearing shaft is held captive in the bearing shaft holder, i.e. in a position in which it cannot be moved back out of the bearing shaft holder through the insertion opening by a translatory movement.

The medical instrument can be constructed in a particularly simple manner if the insertion opening is in the form of a slot opening the bearing shaft holder on one side thereof. The bearing shaft can then be inserted through the slot into the bearing shaft holder in a direction transverse to the pivotal axis.

The bearing shaft can be inserted into the bearing shaft holder in a particularly simple and direct manner if the slot extends away from the pivotal axis in the radial direction.

It is expedient if the slot comprises mutually facing inner surfaces. These can then establish the width of the slot in a simple manner.

The insertion opening can be produced in a particularly simple manner if the inner surfaces run parallel or substantially parallel to a plane containing the pivotal axis. They can then be prepared by a saw-cut or by milling when forming the slot for example.

It is advantageous if the width of the slot is smaller than a diameter defined by the bearing shaft holder. Such a slot enables a suitably formed bearing shaft to be securely held captive in the bearing shaft holder when the instrument is not in the assembly position. It is only when in the assembly position that the bearing shaft can be inserted into or removed from the bearing shaft holder via the slot.

It is expedient if the bearing shaft holder comprises at least one hollow cylindrical inner wall surface section which is concentric with the pivotal axis. An inner wall surface section that has been formed in this way makes it possible for a pivotal movement of the bearing shaft and thus of the e.g. at least one actuating element about the pivotal axis to be guided in a defined manner.

It is advantageous if the bearing shaft comprises at least one cylindrical wall surface section which is concentric with the pivotal axis. It is expedient if two wall surface sections of this type are provided. In particular, cylindrical wall surface sections in cooperation with one or more corresponding hollow cylindrical inner wall surface sections of the bearing shaft holder can lead to a defined pivotal movement of the bearing shaft in the bearing shaft holder.

In accordance with a further advantageous embodiment of the invention, provision may be made for an outer diameter of the bearing shaft which is defined by the at least one cylindrical wall surface section and an inner diameter of the bearing shaft holder which is defined by the at least one inner wall surface section to be mutually matched for play-free or substantially play-free pivoting of the bearing shaft in the bearing shaft holder. This arrangement makes it possible to provide a defined pivotal movement of the at least one actuating element about the pivotal axis.

The bearing shaft can be produced in a particularly simple manner if it is formed from a cylindrical or substantially cylindrical base body and comprises two flattened portions which are laterally spaced from the pivotal axis. The flattened portions can be produced in a simple manner by milling, filing or some other process for machining the base body. In particular, the bearing shaft can be formed in one piece manner with the instrument or the at least one actuating element.

Expediently, the flattened portions run in parallel with each other. In particular, this makes it possible to introduce the bearing shaft in a defined manner, through a slot which laterally opens the bearing shaft holder, into the slot which advantageously may comprise inner surfaces running parallel to each other.

It is advantageous if the spacing of the flattened portions from each other is smaller than the width of the insertion opening. It is then possible to introduce the bearing shaft through the insertion opening into the bearing shaft holder in a defined manner and without jamming.

It is expedient if the instrument comprises an actuating device which comprises the at least one actuating element and a second actuating element which is arranged immovably on the instrument. In particular, such an actuating device makes it possible to hold the instrument securely on the one hand, and to move the at least one tool element in a defined and delicate manner by appropriate manipulation of the at least one actuating element on the other.

It is advantageous if the bearing shaft holder comprises a stop for limiting a pivotal movement of the actuating element in a working position in which the bearing shaft is held captive in the bearing shaft holder. A pivotal movement of the at least one actuating element on the instrument can be limited by the stop in a simple and secure manner.

The stop can be produced in a particularly simple manner if it is in the form of a projection formed on the bearing shaft holder. In particular, it can be formed in one piece manner with the bearing shaft holder.

It is advantageous if the stop defines that position of the actuating elements whereat they are pivoted away from each other to the maximum extent or are pivoted towards one another to the maximum extent. Thus in particular, extreme positions of the actuating elements relative to each other can be defined in a simple manner and the relative movability thereof with respect to one another can be limited.

It is expedient if the stop comprises a stop surface on which a flattened portion of the bearing shaft abuts flatly, at least to a partial extent, in that position in which the actuating elements are pivoted away from each other or towards one another to the maximum extent. Thus in particular, as small a surface pressure as possible can be achieved when the bearing shaft strikes the stop whereby the service life of the instrument can be maximized.

In accordance with one advantageous embodiment of the invention, provision may be made for the at least one actuating element to be in the form of a pivotal branch which comprises a first coupling element that, in a coupling position, is movable into engagement with a second coupling element which is arranged or formed on the at least one tool element or on a force transmission member that is coupled thereto. The first and second coupling elements thus serve, in particular, to directly or indirectly transfer the force that was introduced into the at least one actuating element to the at least one tool element. To this end in particular, the coupling elements may engage with one another with a force-locking and/or positive engagement, whereby they advantageously enable a movement relative to each other, in particular, a translatory and/or a pivotal movement.

It is expedient if the instrument compromises a restoring device for automatically transferring the at least one actuating element from a position in which it is deflected from a basic position back into the basic position, wherein the basic position defines that working position in which the at least one actuating element is rotated though the largest pivotal angle in relation to the assembly position. Thus in particular, the restoring device can prevent the instrument from being transferred into the assembly position in which the bearing shaft can be removed from the bearing shaft holder without the application of an external force, i.e. when it is in the unactuated state. The restoring device thus virtually forms a protecting device for the instrument in order to prevent unintentional dismantling thereof. In particular, it can be formed in such a manner that in the assembly position, the actuating elements of the actuating device are either pivoted towards one another to the maximum extent or they are pivoted away from each other to the maximum extent.

The restoring device can be produced in a particularly simple manner if it comprises at least one restoring member which is supported directly or indirectly on the at least one actuating element or is held thereon. The restoring member can, in particular, be in the form of a spring element which can be designed as a compression or tension member in order to hold the actuating elements towards one another to the maximum extent or away from each other to the maximum extent, without the user having to exert any force on the at least one actuating element. The at least one restoring member can be fixed or fastened to the at least one actuating element by means of a fastening part in the form of a clip or a screw for example. As an alternative or in addition thereto, the at least one restoring member can also be fastened to the at least one actuating element with a force-locking or positive engagement by clamping, for example a free end of the at least one restoring member or another part thereof can engage in a recess or in an undercut in the at least one actuating element with positive or substantially positive engagement and/or be held therein in force-locking manner by being clamped therein.

It is advantageous if the instrument is in the form of a sliding shaft instrument incorporating a sliding shaft which comprises two mutually displacable shaft parts. A large number of medical instruments such as clamps, shears, punches or the like for example can be formed with the aid of such a sliding shaft.

It is expedient if the at least one tool element is arranged or formed at a distal end of the sliding shaft. In connection therewith, for example, this may be a punching tool having a knife-edge which is displacable in the distal or proximal direction and is movable against a corresponding second tool element in the form of an anvil member in order to work on bones or tissue for example.

It is advantageous, if the sliding shaft instrument is in the form of a bone punch. In particular, such a device enables bones and other types of body tissue to be worked on in a simple and defined manner.

Figure 1:
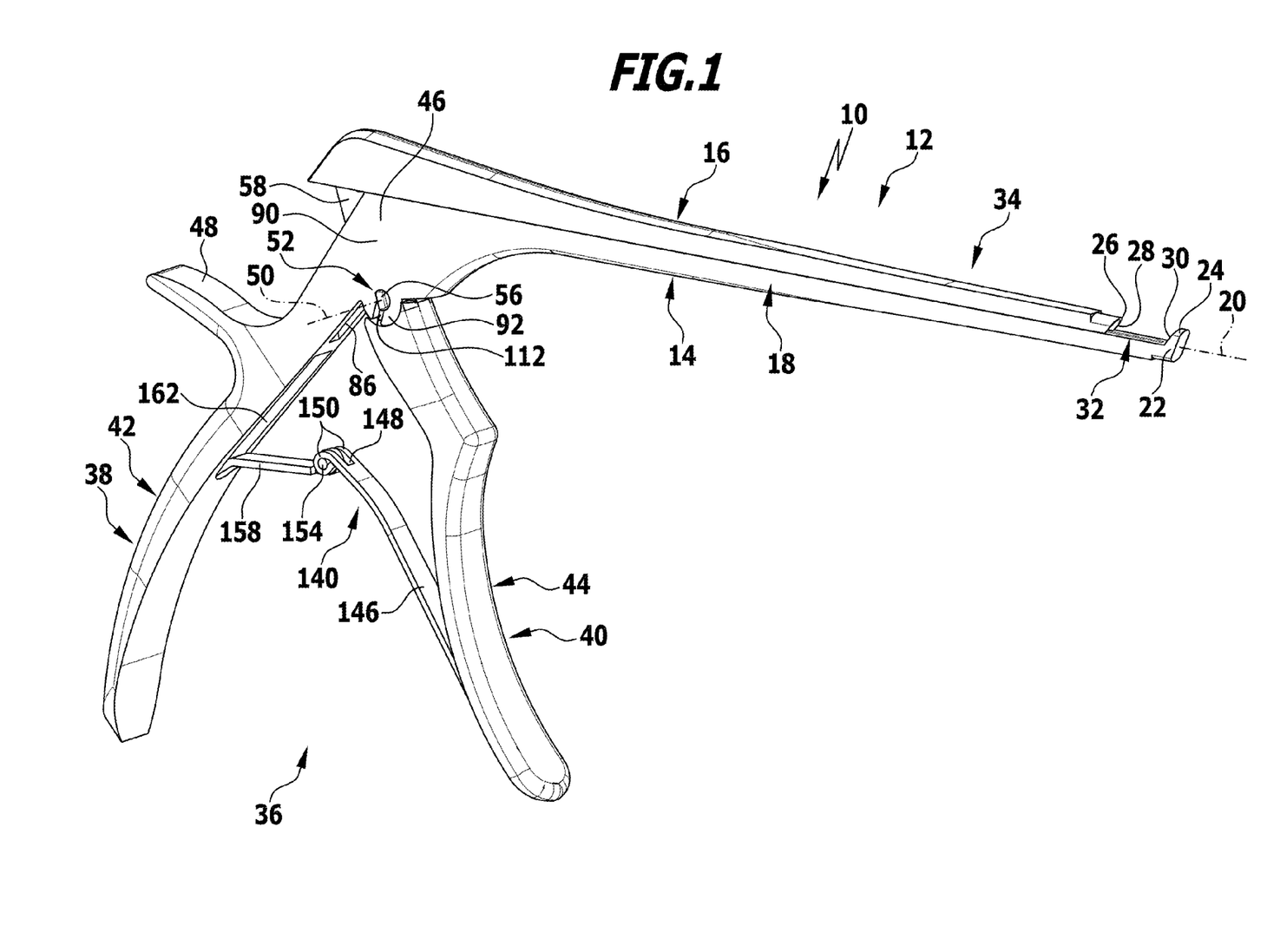
FIG. 1: shows a schematic perspective overall view of a medical instrument in the form of a bone punch.

A medical instrument bearing the general reference symbol 10 is illustrated schematically in FIG. 1. It is in the form of a sliding shaft instrument incorporating a sliding shaft 18 comprising two mutually displacable shaft parts 14 and 16. The shaft parts 14 and 16 are mounted such as to be relatively displacable parallel to the longitudinal axis 20 with the aid of a guidance means which is not illustrated in detail.

At the distal end thereof, the lower shaft part 14 of the sliding shaft 18 carries a projection 22 which points upwardly and projects transversely with respect to a longitudinal axis 20 of the sliding shaft 18 and which forms an anvil 24 for a knife-edge 26 that cooperates therewith and is arranged or formed at a distal end of the upper shaft part 16. The knife-edge 26 forms a first tool element 28 which, together with the anvil 24 forming a second tool element 30, defines a punching device 32 of the instrument 10 forming a bone punch 34.

Furthermore, the instrument 10 comprises an actuating device 36 which incorporates two relatively pivotal branches 38 and 40 which form a respective actuating element 42 and 44 of the actuating device 36. The branch 38 protrudes in a direction transverse to the longitudinal axis 20 from a proximal end of the lower shaft part 14. In particular, the actuating element 42 and the shaft part 14 may be formed in one piece manner. A thumb rest in the form of a projection pointing in the proximal direction protrudes from the branch 38. Overall then, the branch 38 is arranged on the instrument 10 such as to be immovable.

The branch 40 is mounted such that it is pivotal relative to the branch 38 about a pivotal axis 50. For this purpose, the instrument 10 comprises a pivotal bearing 52 comprising a bearing shaft holder 54 and a bearing shaft 56 which is rotatable or pivotal therein about the pivotal axis 50. The bearing shaft 56 is formed on a plate-like coupling section 58 of the actuating element 44 and protrudes from a side face thereof. It is formed of a cylindrical base body 60 and has two flattened portions 62 and 64 which define side faces 66 and 68 that run in parallel with one another.

At the free end 70 thereof, the coupling section 58 comprises a slot-like recess 72 having a width 74 which corresponds to an outer diameter 76 of a coupling stud 78 that is arranged or formed on the shaft part 16. The cylindrical coupling stud 78 is arranged transversely of the longitudinal axis 20 in a recess 80 of the shaft part 16 which is open towards the shaft part 14. The end 70 is rounded in the form of a semicircle. The width of the recess 80 corresponds to the thickness 82 of the coupling section 58 so that the latter is guided laterally in the recess 80.

At the end 46, i.e. in the transitional region between the shaft part 14 and the actuating element 42, there is formed a mounting section 84 which comprises a through hole 86. The through hole 86 is closed by lateral wall regions 88 and 90 and opens up the mounting section 84 in the upward direction to the downwardly open recess 80, both proximally as well as downwardly. Mounting cheeks 92 and 94 project downwardly from the wall regions 88 and 90, these cheeks being semicircular when viewed from the side. The width of the through hole 86 corresponds to the thickness 82 of the coupling section 58 so that it can be introduced through the through hole 86, and the coupling stud 78 and the recess 72 which form the coupling elements 96 and 98 are movable into engagement with one another.

The bearing shaft holder 54 is formed on the mounting cheeks 92. It comprises a hollow cylindrical inner wall surface section 100 which extends over a peripheral angle 102 of approximately 210°. A diameter 104 of the bearing shaft holder defined by the inner wall surface section 100 corresponds to an outer diameter 110 defined by two cylindrical wall surface sections 106 and 108 of the bearing shaft 56 which are located diametrically opposite each other with respect to the pivotal axis 50.

The bearing shaft holder 54 is opened laterally, namely, in a direction transverse to the pivotal axis 50, by an insertion opening 112. This is in the form of a slot 114 which opens the bearing shaft holder 54 on one side. It extends away from the pivotal axis 50 in the radial direction. The slot 114 comprises two mutually facing inner surfaces 116 and 118 which run in parallel with each other and with a plane 120 containing the pivotal axis 50. The inner surfaces 116 are spaced from each other by a distance which corresponds to the width 170 of the slot 114. The width 170 corresponds to the spacing of the side faces 66 and 68 from each other. The bearing shaft 54 can thus be pushed into the bearing shaft holder 54 through the slot 114.

Figure 2:
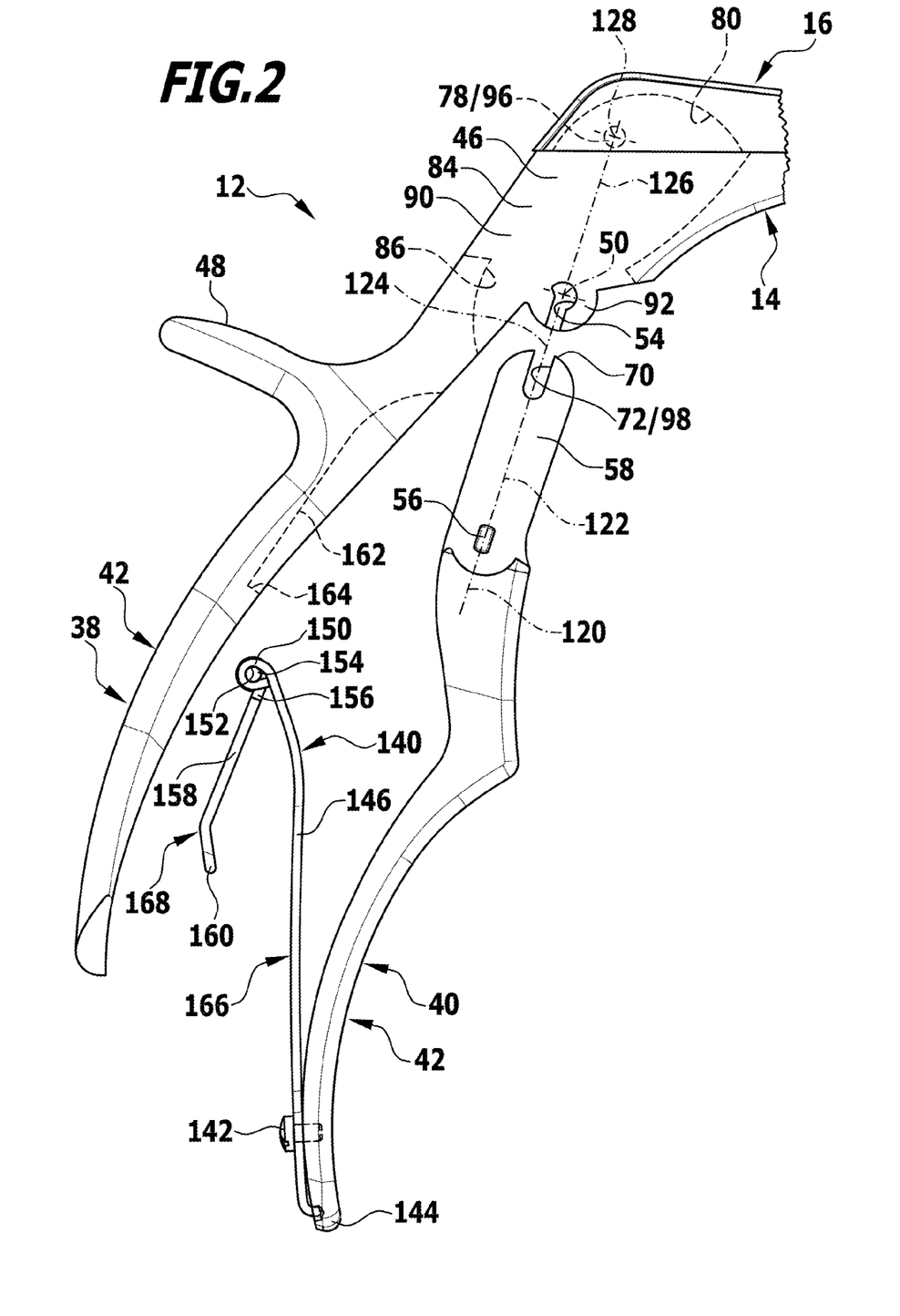
FIG. 2: a partly cut-away side view of the instrument illustrated in FIG. 1 before the assembly of an actuating element.
Figure 3:
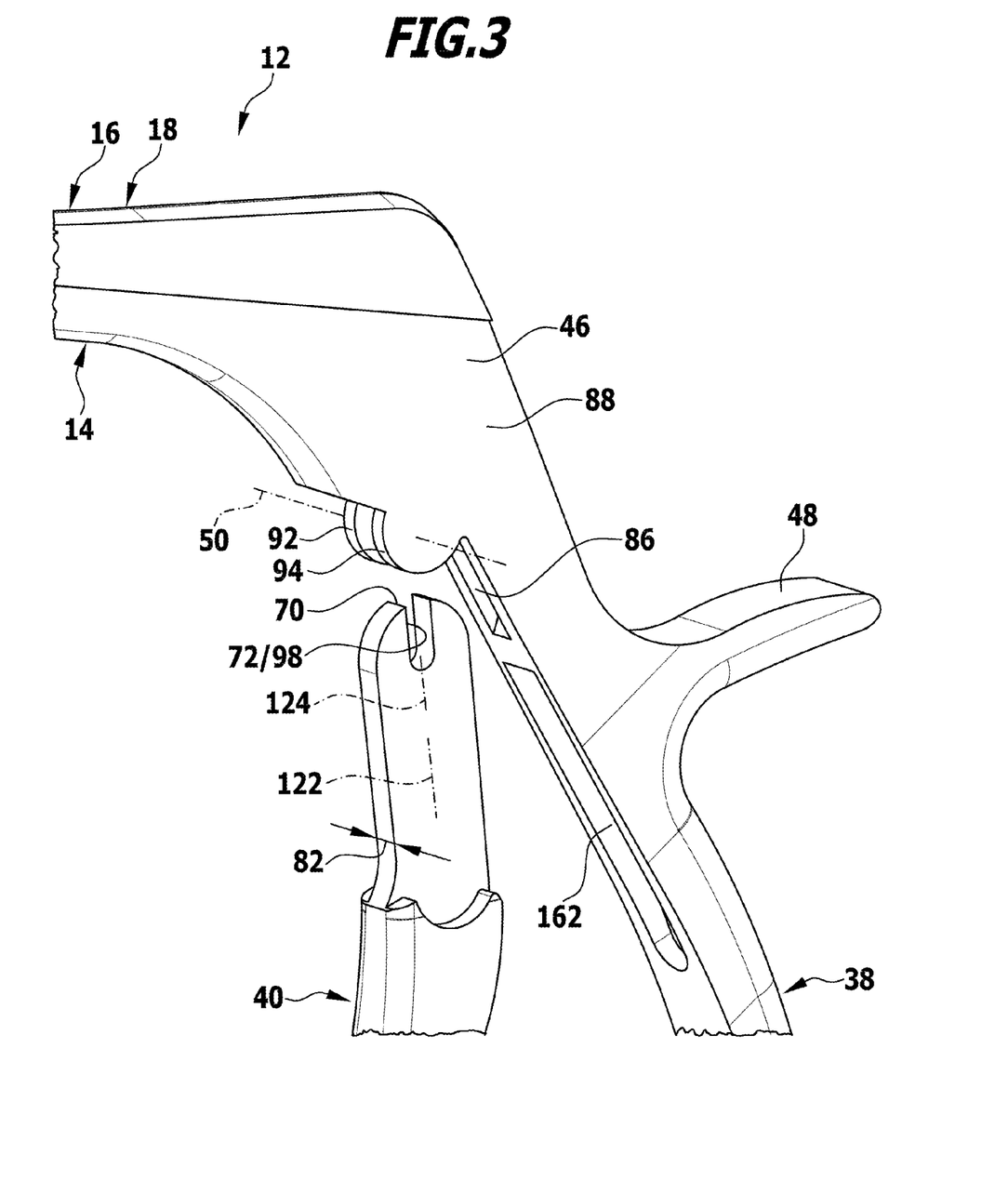
FIG. 3: a partial perspective view of a part of the instrument illustrated in FIG. 2 from the opposite side.

The bearing shaft 56 is arranged on the coupling section 58 in such a manner that it defines a longitudinal axis 122 which coincides with a longitudinal axis 124 defined by the recess 72. The slot 114 likewise defines a longitudinal axis 126 which intersects a longitudinal axis 128 of the coupling stud 78. The described alignment of the longitudinal axes 122 and 124 as well as 126 and 128 makes it possible for the coupling section 58 to be brought into engagement with the mounting section 84 when in an assembly position such as is illustrated schematically in FIG. 2. In the assembly position, the longitudinal axes 122 and 126 are aligned in parallel with each other so that the bearing shaft 56 is insertable into the bearing shaft holder 54 through the slot 114 by means of a purely translatory movement and the coupling stud 78 is insertable into the recess 72 at the same time.

Figure 4:
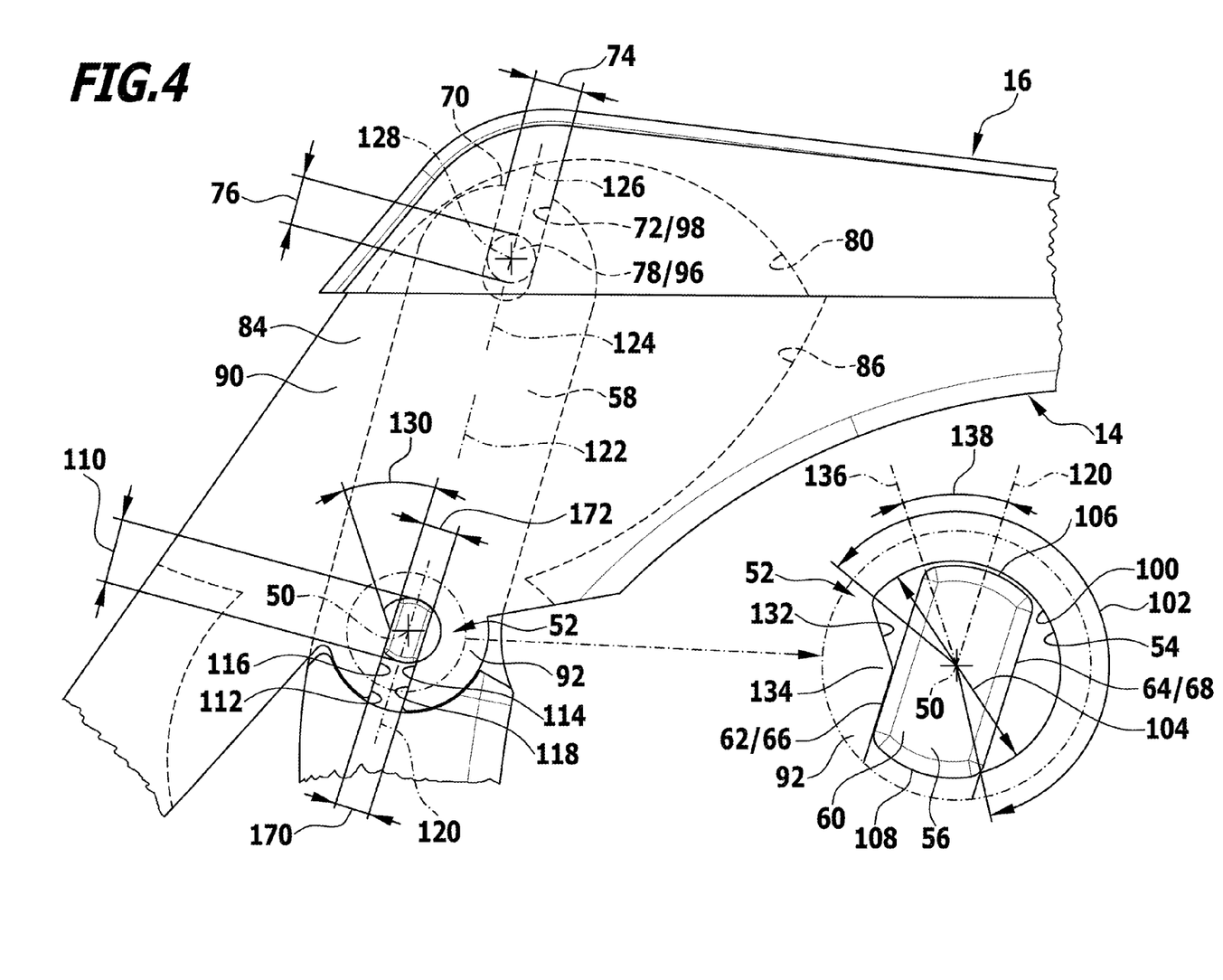
FIG. 4: a partly cut-away view of a part of the instrument including a bearing shaft of the actuating element inserted into a bearing shaft holder thereof in the assembly position.

Once the bearing shaft 56 has been fully inserted into the bearing shaft holder 54 as is schematically illustrated in FIG. 4, then, as a result of the selected dimensions of the diameter 104 and the outer diameter 110, it is possible for the actuating element 44 to pivot about the pivotal axis 50, namely, through a maximum pivotal angle 130 which, in the assembly position, is defined between the side face 66 and a stop surface 132 of a stop 134 which is formed on the bearing shaft holder 54 in the form of a projection. This stop is provided for limiting a pivotal movement of the actuating element 44 about the pivotal axis 50. The stop surface 132 defines a plane which runs in parallel with a further plane 136 containing the pivotal axis 50. The planes 120 and 136 likewise define therebetween a pivotal angle 138 which corresponds to the pivotal angle 130.

Furthermore, the instrument 10 comprises a restoring device 140 against the effect of which the actuating element 44 can be pivoted in the direction of the actuating element 42. The restoring device 140 comprises a leaf spring 146 which is fixed to a free end 144 of the branch 40 by means of a screw 142 and is provided at the other free end thereof with a slot 148 thereby leaving two protruding projections 150 which are each rolled up so as to form a seating 152 or eye for a mounting pin 154 that is formed at a free end 156 of a second leaf spring element 158 and engages in the seatings 152 so that the leaf spring element 158 and the leaf spring 146 are pivotal relative to each other about a pivotal axis defined by the mounting pin 154. As an alternative or in addition thereto, the free end 144 of the leaf spring 146 can also be fixed to the branch 40 with a force-locking or positive engagement by clamping, for example the free end 144 of the leaf spring 146 or another part thereof can engage in a recess that is not illustrated in detail in the Figures or in an undercut in the branch 40 with positive or substantially positive engagement and/or be held therein in force-locking manner by being clamped therein.

Figure 5:
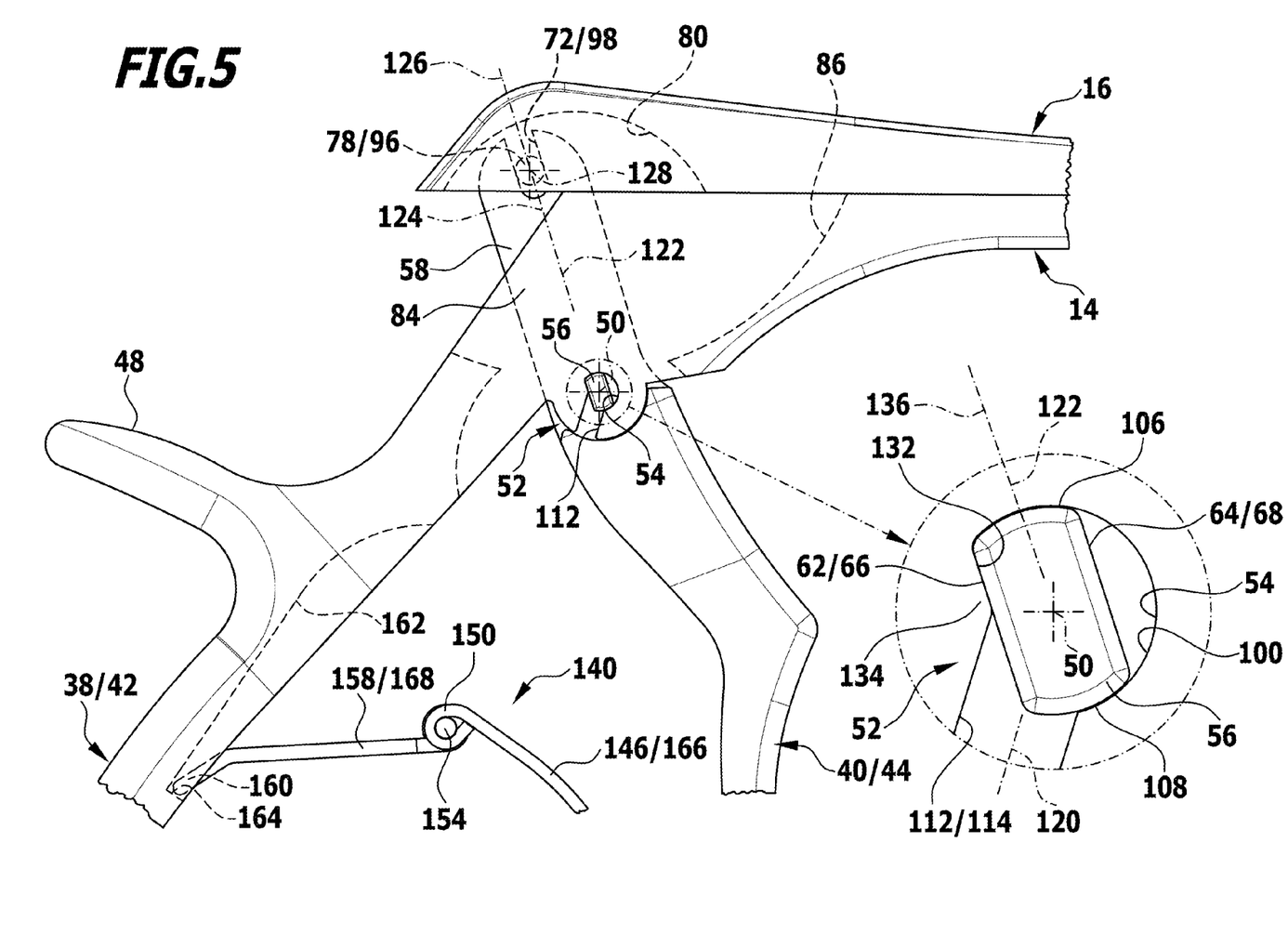
FIG. 5: a partly cut-away view of a part of the instrument in the working position wherein the actuating elements are pivoted away from each other to the maximum extent.
Figure 6:
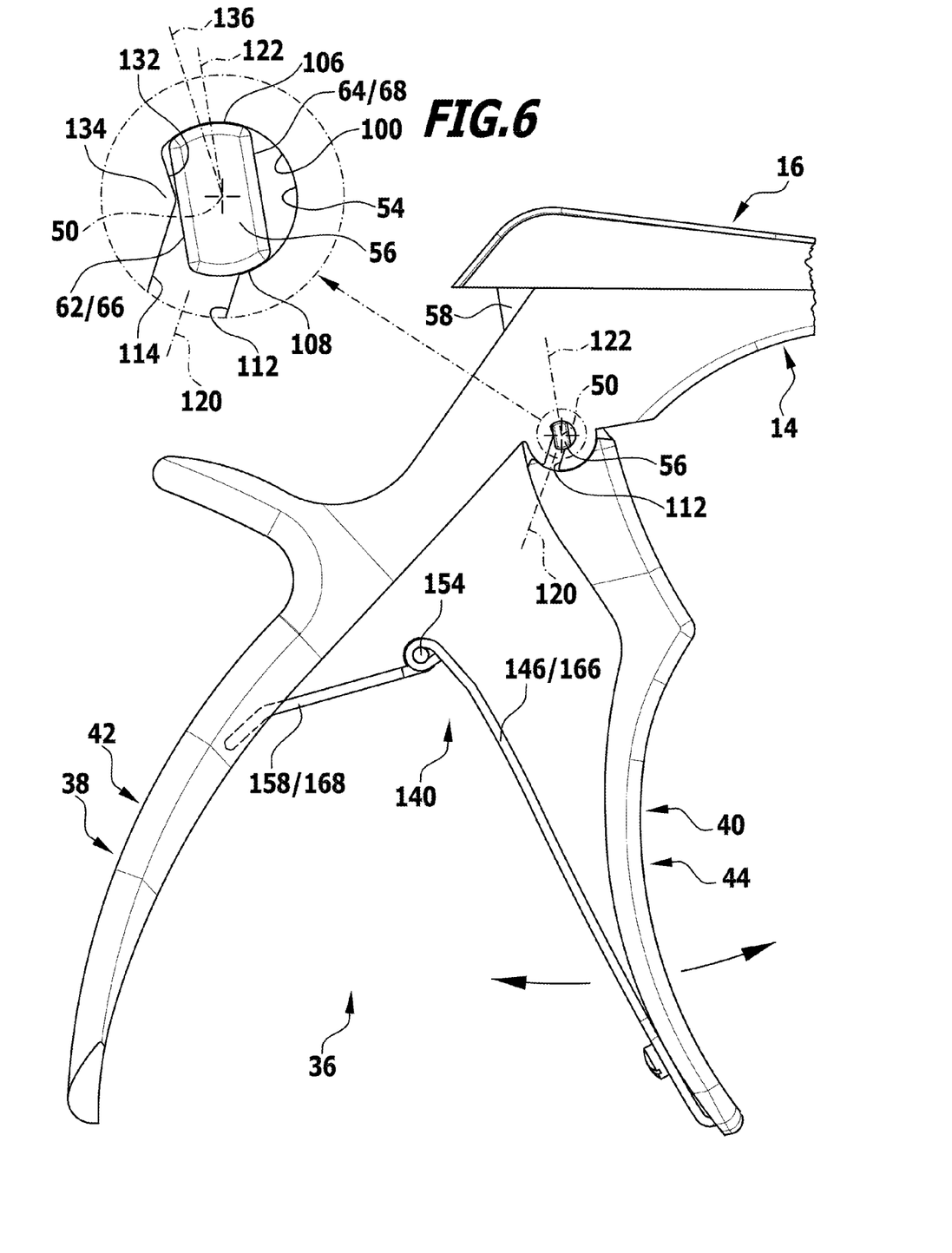
FIG. 6: a side view of the instrument in a working position wherein the actuating elements are pivoted somewhat towards one another.

The leaf spring element 158 is slightly bent at its other free end 160 and projects into a recess 162 in the actuating element 42. The recess 162 has a stop surface 164 which faces in the direction of the shaft part 16. The end 160 abuts against the stop surface 164 in the recess 162. The restoring device 140 comprising the leaf spring 146 and the leaf spring element 158 which form the respective restoring members 166 and 168 keeps the two actuating elements 42 and 44 in a basic position that is illustrated schematically in FIG. 5 in which they are pivoted away from each other to the maximum extent. In this basic position, the flattened portion 62 abuts against the stop surface 132 and thus limits a movement of the branch 40 away from the branch 38. The branch 40 can now be pivoted against the effect of the restoring device 140 towards the branch 38. As long as the pivotal angle in the working position in which the bearing shaft 56 is held captive in the bearing shaft holder 54 is smaller than the pivotal angle 130, the bearing shaft 56 cannot escape from the bearing shaft holder 54 through the slot 114.

The particular configuration of the pivotal bearing 52 makes it possible to assemble the instrument 10 without tools in a simple manner. Thus the bearing shaft 46 is merely inserted into the bearing shaft holder 54. The pivotal bearing is thus virtually screw-less.

It is also conceivable in principle for the pivotal bearing 52 described above in connection with a bone punch 34 to be usable in any hand grip of a medical instrument which comprises two relatively pivotal actuating elements. In particular, such a hand grip of the instrument may be connectable to a shaft thereof in releasable manner for example as is often the case with endoscopic tubular shaft instruments.

What is claimed is:

1. A medical instrument, comprising:
   at least one movable tool element,
   at least one actuating element which is mounted so as to be pivotal about a pivotal axis, the at least one actuating element being directly or indirectly coupled to the at least one tool element for moving the at least one tool element as a result of a pivotal movement of the at least one actuating element, and
   a pivotal bearing for the pivotal mounting of the at least one actuating element, the pivotal bearing comprising a bearing shaft holder and a bearing shaft which is held in the bearing shaft holder in a working position,
   wherein:
   the at least one actuating element incorporates the bearing shaft or the bearing shaft holder,
   the bearing shaft holder has an insertion opening,
   in an assembly position, the bearing shaft is insertable through the insertion opening into the bearing shaft holder in a direction that is transverse or substantially transverse to the pivotal axis,
   the bearing shaft holder comprises a stop for limiting a pivotal movement of the at least one actuating element in the working position in which the bearing shaft is held captive in the bearing shaft holder,
   the at least one actuating element comprises two actuating elements, and
   the stop comprises a stop surface on which a flattened portion of the bearing shaft abuts flatly at least to a partial extent in a position in which the two actuating elements are pivoted away from each other or towards one another to a maximum extent.

2. The medical instrument in accordance with claim 1, wherein the bearing shaft that has been inserted into the bearing shaft holder is movable from the assembly position into the working position in which the bearing shaft is held captive in the bearing shaft holder by pivoting it about the pivotal axis.

3. The medical instrument in accordance with claim 1, wherein the insertion opening is in the form of a slot opening the bearing shaft holder on one side thereof.

4. The medical instrument in accordance with claim 3, wherein the slot extends away from the pivotal axis in a radial direction.

5. The medical instrument in accordance with claim 3, wherein the slot comprises mutually facing inner surfaces.

6. The medical instrument in accordance with claim 5, wherein the inner surfaces run parallel or substantially parallel to a plane containing the pivotal axis.

7. The medical instrument in accordance with claim 3, wherein the slot has a width which is smaller than a diameter defined by the bearing shaft holder.

8. The medical instrument in accordance with claim 1, wherein bearing shaft holder comprises at least one hollow cylindrical inner wall surface section which is concentric with the pivotal axis.

9. The medical instrument in accordance with claim 1, wherein an outer diameter of the bearing shaft which is defined by at least one cylindrical wall surface section, and an inner diameter of the bearing shaft holder which is defined by at least one inner wall surface section are mutually adapted for play-free or substantially play-free pivoting of the bearing shaft in the bearing shaft holder.

10. The medical instrument in accordance with claim 1, wherein the bearing shaft comprises at least one cylindrical wall surface section which is concentric with the pivotal axis.

11. The medical instrument in accordance with claim 1, wherein the bearing shaft is formed from a cylindrical or substantially cylindrical base body and has two flattened portions which are laterally spaced from the pivotal axis.

12. The medical instrument in accordance with claim 11, wherein the flattened portions run in parallel with each other.

13. The medical instrument in accordance with claim 11, wherein a spacing of the flattened portions from each other is smaller than a width of the insertion opening.

14. The medical instrument in accordance with claim 1, further comprising an actuating device which comprises the two actuating elements,
the two actuating elements comprising a first actuating element which is movable and a second actuating element which is arranged immovably on the instrument.

15. The medical instrument in accordance with claim 1, wherein the stop is in the form of a projection that is formed on the bearing shaft holder.

16. The medical instrument in accordance with claim 1, wherein the stop defines the position of the two actuating elements in which they are pivoted away from each other or towards one another to the maximum extent.

17. The medical instrument in accordance with claim 1, wherein the at least one actuating element is in the form of a pivotal branch which comprises a first coupling element which, in a coupling position, is movable into engagement with a second coupling element which is arranged or formed on the at least one tool element or on a force transmission member that is coupled thereto.

18. The medical instrument in accordance with claim 1, further comprising a restoring device for automatically transferring the at least one actuating element from a position in which it is deflected from a basic position back into the basic position, wherein the basic position defines the working position in which the at least one actuating element is rotated though a largest pivotal angle in relation to the assembly position.

19. The medical instrument in accordance with claim 18, wherein the restoring device comprises at least one restoring member which is supported directly or indirectly on the at least one actuating element or is held thereon.

20. The medical instrument in accordance with claim 1, wherein the instrument is in the form of a sliding shaft instrument incorporating a sliding shaft comprising two mutually displacable shaft parts.

21. The medical instrument in accordance with claim 20, wherein the at least one tool element is arranged or formed at a distal end of the sliding shaft.

22. The medical instrument in accordance with claim 20, wherein the sliding shaft instrument is in the form of a bone punch.

23. The medical instrument in accordance with claim 1, wherein the bearing shaft is formed in a one piece manner with the instrument or the at least one actuating element.

* * * * *